United States Patent [19]

Ostertag et al.

[11] Patent Number: 4,848,864
[45] Date of Patent: Jul. 18, 1989

[54] SCANNER FOR THE OPTICAL SCANNING OF OBJECTS

[75] Inventors: Klaus Ostertag, Munich; Karl Pietzsch, Geretsried, both of Fed. Rep. of Germany

[73] Assignee: Erwin Sick GmbH Optik-Electronik, Fed. Rep. of Germany

[21] Appl. No.: 125,301

[22] Filed: Nov. 25, 1987

[30] Foreign Application Priority Data

Jan. 12, 1987 [DE] Fed. Rep. of Germany ....... 8700520

[51] Int. Cl.$^4$ .............................................. G02B 26/10
[52] U.S. Cl. ..................................... 350/6.8; 350/6.7; 250/235
[58] Field of Search ................... 350/6.5, 6.6, 6.7, 6.8, 350/163, 164; 250/234, 235, 236; 356/363, 431; 358/208; 369/58

[56] References Cited

U.S. PATENT DOCUMENTS

| 4,199,219 | 4/1980 | Suzki et al. | 350/6.8 |
| 4,291,987 | 9/1981 | Sick et al. | 350/6.8 |
| 4,357,071 | 11/1982 | Mankel et al. | 350/6.8 |
| 4,629,885 | 12/1986 | Asemyr | 350/6.8 |

Primary Examiner—Rodney B. Bovernick
Assistant Examiner—Loha Ben
Attorney, Agent, or Firm—Townsend and Townsend

[57] ABSTRACT

In a scanner for the optical checking of objects such as CD-discs there is provided a coherent light source; a light deflecting device which allows a light beam emitted from the light source to sweep over the object in a substantially linear scanning movement, with the optical axis of the light beam subtending a small angle with a normal to the object surface transverse to the scanning direction; and a detector for detecting light which is reflected back from the object. In the present arrangement the optical axis of the light beam also subtends a small angle with the normal to the object surface in the scanning direction. This makes it possible to avoid disturbing modulation of the detector signal due to interference effects.

9 Claims, 5 Drawing Sheets

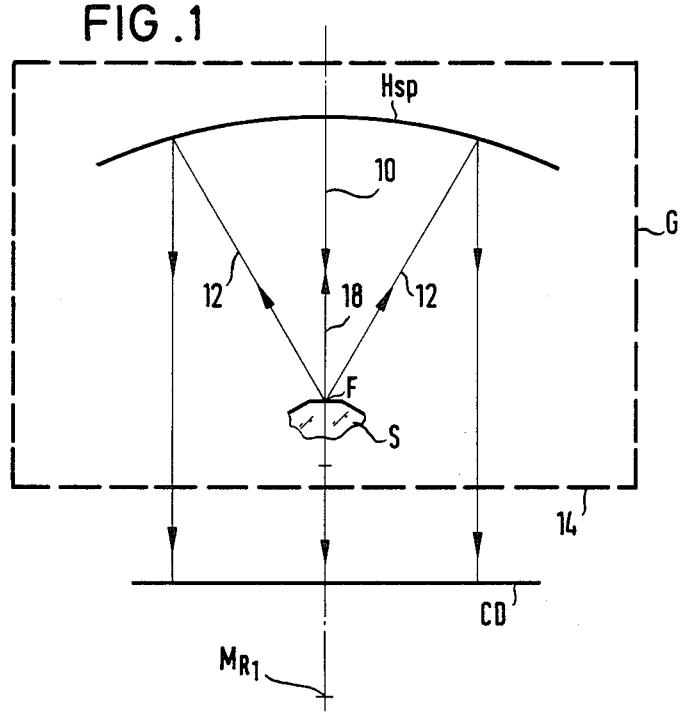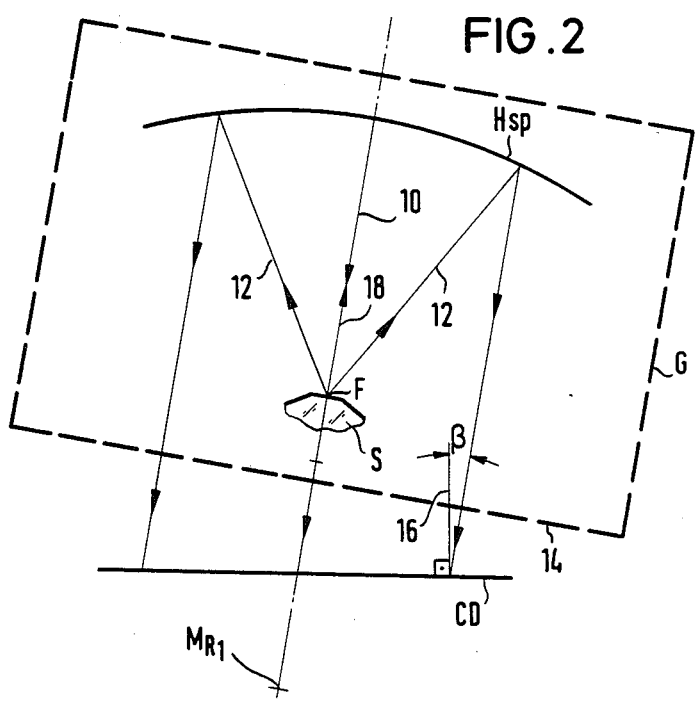

SCANNER FOR THE OPTICAL SCANNING OF OBJECTS

BACKGROUND OF THE INVENTION

The invention relates to a scanner for the optical scanning of objects, in particular recording discs, comprising a coherent light source; a light deflecting device which allows a light beam emerging from the light source to sweep over the object in a substantially linear scanning movement, with the optical axis of the light beam subtending a small angle with a normal to the object surface transverse to the scanning direction; and a detector for detecting light which is reflected back from the object.

Such scanners are used in the cheking of CD recording discs (compact discs) which accompanies the production thereof. Compact discs are metallized plastic discs coated with a transparent protective layer with a digital information, in particular an audio signal or a video signal being accommodated on the metallized plastic discs in the form of microscopic elevations and depressions. For the replay the CD recording discs are read out with a laser beam which is reflected at the metallic layer. A scanner used in the inspection of CD recording discs operates in accordance with the same principle. This makes it possible to scan the disc surface without gaps using a rapidly deflected laser beam with simultaneous rotation of the disc, and thereby to detect disc faults which produce a change of the reflected and/or diffracted laser light.

It is known to allow the coherent laser light to be incident on the CD recording disc perpendicular to the scanning direction as seen in the scanning direction parallel to the normal to the disc, but at a small angle to the normal onto the disc. The angle serves in this arrangement for the separation of the incident light and the light reflected back by the disc. This angle is small, for example about 1.5°, so that no notable enlargement of the light bead occurs above the reflective metal surface and transverse to the scanning direction through the separation of the incident and reflected light, and so that a correspondingly high measurement accuracy and fault sensitivity is also achieved for faults above the metal surface—in the substrate or at the read-out side.

The incident laser beam penetrates the about 1.2 mm thick plastic layer of the CD recording disc and is reflected from the metallic reflective coating lying beneath it. During this the information pattern of the CD disc, which acts as diffraction grating, generates several discrete diffraction orders. The reflected light of the zero diffraction order and of the discrete higher diffraction orders is multiply reflected at the boundary surfaces between air and plastic on the one hand and plastic and plastic at the reflective coating on the other hand, with each laser beam generating discrete diffraction orders anew on reimpingement on the information tracks of the CD recording disc. In this manner, with corresponding geometry of the boundary surfaces relative to one another, a superposition of light beams causes interference fringes of constant thickness. This leads to significant modulation of the received signal generated by the reflected and/or diffracted light coming from the disc. This in turn makes the detection of manufacturing faults in the CD recording disc more difficult and reduces the accuracy of the testing method.

SUMMARY OF THE INVENTION

The object underlying the invention is to provide a scanner which can be used to inspect CD recording discs in which interference, which leads to modulation of the received signal is suppressed in an effective manner without notably impairing the accuracy of the fault location.

In order to satisfy this object it is proposed that the optical axis of the light beam also subtend a small angle in the scanning direction with the normal to the surface of the object to be scanned.

The optical axis of the light beam subtends a small angle with a normal to the surface of the object, such that the subtended angle produces two other inclined angles which are projections of the subtended angle onto two perpendicular planes containing the normal, at the impingement point, to the surface of the object being scanned. One of the two produced inclined angles extends in a direction transverse to the scanning direction.

The laser beams which are reflected to and fro between the boundary surfaces of the CD recording disc are spatially separated by the angle subtended to the normal in the scanning direction. In this way the disturbing interference effects disappear.

The use of an incident light beam which subtends an angle different from zero with the normal in the scanning direction leads to an apparent broadening of the light bead in the scanning direction through the small spatial separation of the incident and reflected beam, and thus to an apparent broadening of the fault in this direction, in particular for defects near the disc surface. This apparent broadening of the fault does not however play a decisive role for the inspection result. Any small defocussing which may eventually be caused at the start and end of the scanning range by the slightly oblique light incidence in the scanning direction is of negligible effect during the inspection of a CD recording disc.

Alternatives exist to the solution proposed in accordance with the invention. For example it is conceivable that the chromatic coherence of the light source could be disturbed. This would however make it necessary to replace the laser by an incoherent light source, which would bring numerous disadvantages, in particular a deterioration of the signal quality. Furthermore, one could think of disturbing the spatial coherence of the light source, this however gives rise to similar disadvantages and this process is not practicable, at least at the high sampling frequencies of about 10 MHz (scan frequency about 3 kHz) which is necessary here for reading out the scanner video signals.

A further alternative to the solution of the invention lies in increasing the angle which the laser beam subtends transverse to the scanning direction with the normal to the surface of the object to be scanned, with incidence viewed in the scanning direction remaining unchanged in the normal direction. The laser beams which are reflected to and fro between the boundary surfaces of the CD recording disc are likewise only spatially separated, so that the interference effects disappear, at an adequately large angle, in particular at an angle of incidence of more than 5°. A relatively large angle of incidence perpendicular to the scanning direction results however in an apparent fault elongation in the track direction for faults within the transparent plastic layer, and in particular faults lying near the disc surface, because the incident and spatially separated reflected beam detect the fault one after the other. The accuracy of fault recognition, i.e. the evaluation of the length of the fault is thereby impaired.

The proposal of the invention that the laser beam should be inclined at a small angle to the normal to the surface of the object to be scanned both transverse to the scanning direction and also in the scanning direction is free of the disadvantages of the variants discussed above. In particular both angles can be selected to be very small so that the resulting apparent increase in size of the fault does not play any notable role. In a preferred development the optical axis of the light beam subtends a maximum angle in the scanning direction of 3° with the normal to the surface of the object to be scanned.

The optical scanner of the invention can contain a deflecting device which includes a rotationally driven polygonal mirror wheel with peripheral mirror surfaces. The scanner also contains a concave mirror which lies in the beam path between the mirror wheel and the object. The concave mirror can in this arrangement be formed as a concave mirror strip having preferably a spherical or regular cylindrical concave mirror surface. Alternatively, an objective including at least one lens may be used instead of a concave mirror, the objective lying in the beam path between the mirror wheel and the object.

A telecentric construction of a scanner of this kind is possible in which the mirror surface of the mirror wheel on which the light beam impinges lies at the focal point of the concave mirror. In order to provide, with a telecentric scanner of this kind, the slightly inclined incidence of the laser beam in the scanning direction in accordance with the invention one places the scanner as a whole at the desired angle in the scanning direction relative to the object to be scanned. This can take place by tilting the entire scanner relative to the object to be scanned, or by tilting this object relative to the scanner. An advantage of this construction is the fact that a customary telecentric scanner can be used without changing its internal consturction, only a change of its mounting is necessary. The appearance of the overall arrangement is however unusual.

In further variants of the invention it is proposed, starting from a telecentric scanner of the named kind, that the relative position of the mirror wheel and concave mirror should be slightly modified in order to achieve the desired slightly oblique incidence of the laser beam in the scanning direction. For this purpose one can defocuss the telecentric scanner so that the concave mirror is inclined at a small angle relative to the mirror wheel in the scanning direction when compared with the telecentric arrangement. Another defocussing possibility consists in displacing the concave mirror in parallel relative to the mirror wheel in the scanning direction when compared with its telecentric position. Both variants can also be combined with one another and it will be understood that it is only the relative optical position of the concave mirror wheel which is important, so that one can also obtain a comparable result by changes of an optical system lying therebetween. An advantage of corresponding constructionally amended scanners is the fact that they appear from the outside to be customary telecentric scanners, and can be handled in precisely the same way, however with the disturbing interference effects being suppressed by the oblique incidence of the light in the scanning direction.

The invention will be explained in more detail with reference to the embodiments which are illustrated in the drawings.

BRIEF DESCRIPTION OF THE DRAWINGS

FIG. 1 shows the scanning plane of a telecentric scanner which directs a laser beam perpendicularly onto the surface of an object to be scanned as seen in the scanning direction;

FIG. 2 shows the scanning plane of a telecentric scanner which, when compared with FIG. 1, is inclined as a whole relative to the object to be scanned, so that the laser beam includes an angle with the surface normal to the object to be scanned as seen in the scanning direction;

DETAILED DESCRIPTION OF THE PREFERRED EMBODIMENT

Figure 3:
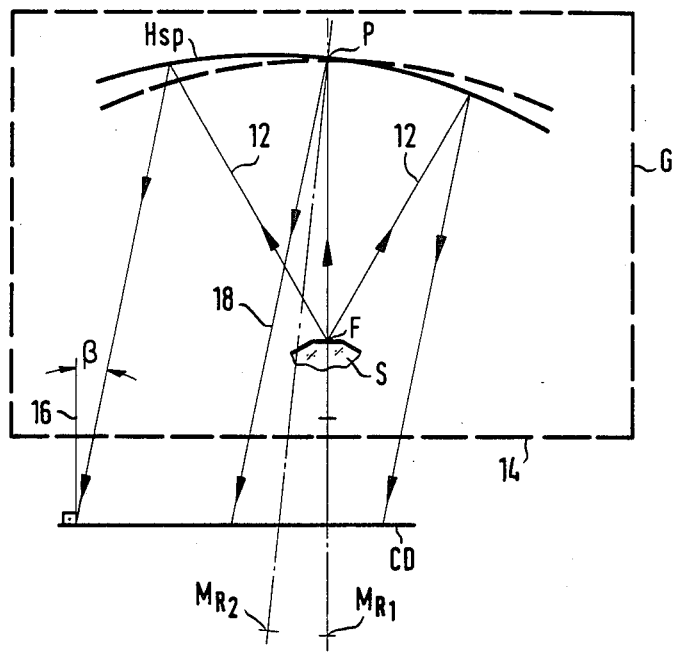
FIG. 3 shows the scanning plane of a scanner which, starting with the telecentric arrangement has been defocussed by tilting of the concave mirror in the scanning direction.

FIG. 1 shows a telecentric scanner with which an object, in particular a recording disc CD is scanned. The scanner has a housing G in which a mirror wheel S and a concave mirror Hsp are located. The mirror wheel S, which is only shown in section, is a polygonal mirror which is driven so that it rotates about its centerpoint. Facet like mirror surfaces are provided at the periphery of the mirror wheel S. One of the mirror surfaces is hit by an incident light beam 10.

The concave mirror Hsp is arranged parallel to the scanning direction in the housing G. It is constructed as a concave mirror strip. $M_{R2}$ is the geometrical center of the concave mirror Hsp.

The effective mirror surface of the mirror wheel S is located at the focal point F of the concave mirror Hsp, i.e. at the half distance between its geometrical center $M_{R1}$ and the concave mirror surface. The divergent scanning rays 12 reflected from the mirror wheel S are thus rendered parallel by the concave mirror Hsp. They leave the housing G, the lower edge 14 of which is aligned parallel to the object CD to be scanned, and impinge perpendicularly onto the surface of the object CD as seen in the scanning direction. The object is thus repeatedly swept over linearly by the laser beam on rotation of the mirror wheel S. In the event of inspection of CD recording discs (compact discs) the previously mentioned interference and modulation of the received video signal occur.

In order to overcome this it is proposed, in accordance with FIG. 2, that the telecentric scanner and the object CD to be scanned be inclined relative to one another in the scanning direction. In the drawing, the housing G of the scanner is tilted relative to the recording disc CD so that the lower edge 14 of the housing subtends an acute angle with the surface of the recording disc CD which is to be scanned. It is naturally also possible to correspondingly pivot the recording disc CD or its mount. The internal construction of the scanner is not changed relative to FIG. 1. One recognizes that the light beams emerging from the housing G now subtend an angle $\beta$ which differs from zero with the normal 16 to the scanning surface as seen in the scanning direction. The angle $\beta$ is small, it amounts to a maximum value of about 3°. As a result of this slight inclined incidence of the laser light in the scanning direction one prevents interference at the thin layers, and thus the resulting modulation of the signal obtained on inspection of CD recording discs.

Figure 4:
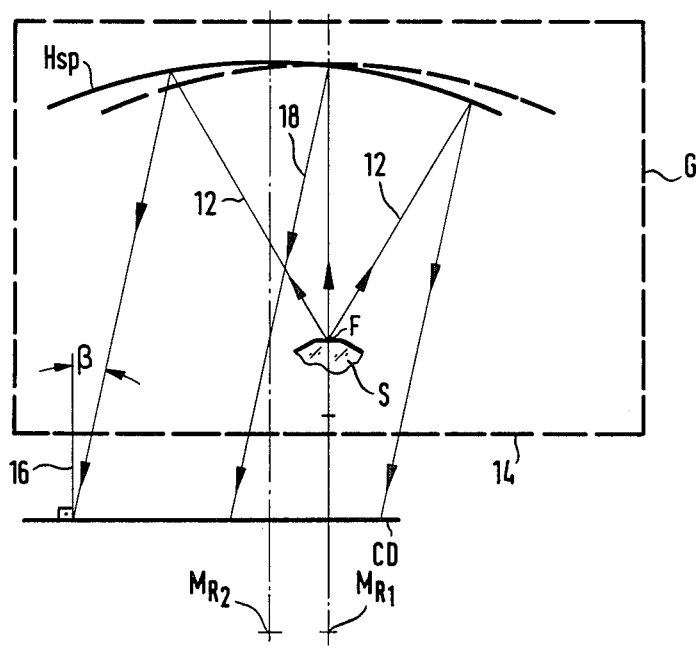
FIG. 4 shows the scanning plane of a scanner which, starting from the telecentric arrangement has been defocussed by a parallel displacement of the concave mirror in the scanning direction.

In the variants of FIGS. 3 and 4 on the scanner housing is aligned parallel to the object to be scanned and the scanner is in each case slightly defocussed or out of alignment when compared with the telecentric arrangement of FIG. 1. In FIG. 3 the concave mirror Hsp is rotated about an axis P which is orientated parallel to the axis of rotation of the mirror wheel S and is located at the position of the concave mirror surface at which the central ray 18 reflected from the mirror wheel S impinges on the concave mirror Hsp. The central ray 18 is thereby no longer reflected back on itself but is on the contrary displaced either in the scanning direction or against the scanning direction. As a result, the laser beams as seen in the scanning direction impinge onto the surface of the object CD to be scanned at an angle which differs from 90° and the interference effects which can be observed with normal incidence disappear. In distinction to the telecentric arrangement of FIG. 1 the effective mirror surface of the mirror wheel S does not lie precisely at the focus of the concave mirror Hsp which leads to small focussing errors at the end of the scanning range. These do not however notably impair the scanning result, in particular when inspecting CD recording discs.

In FIG. 4 the concave mirror Hsp is laterally displaced either in the scanning direction or against the scanning direction starting from the telecentric arrangement of FIG. 1. The geometrical center of the concave mirror Hsp is thereby displaced from $M_{R1}$ to $M_{R2}$. As the connection line between the geometrical center and the beam impingement point on the concave mirror forms the bisector of the angle between the incident and the emergent beam the beams are also deflected in this case in such a way that they impinge onto the object to be scanned at an angle different from 90°. In this way the interferences which occur with normal beam incidence are suppressed, without notable imaging errors occurring.

Figure 5:
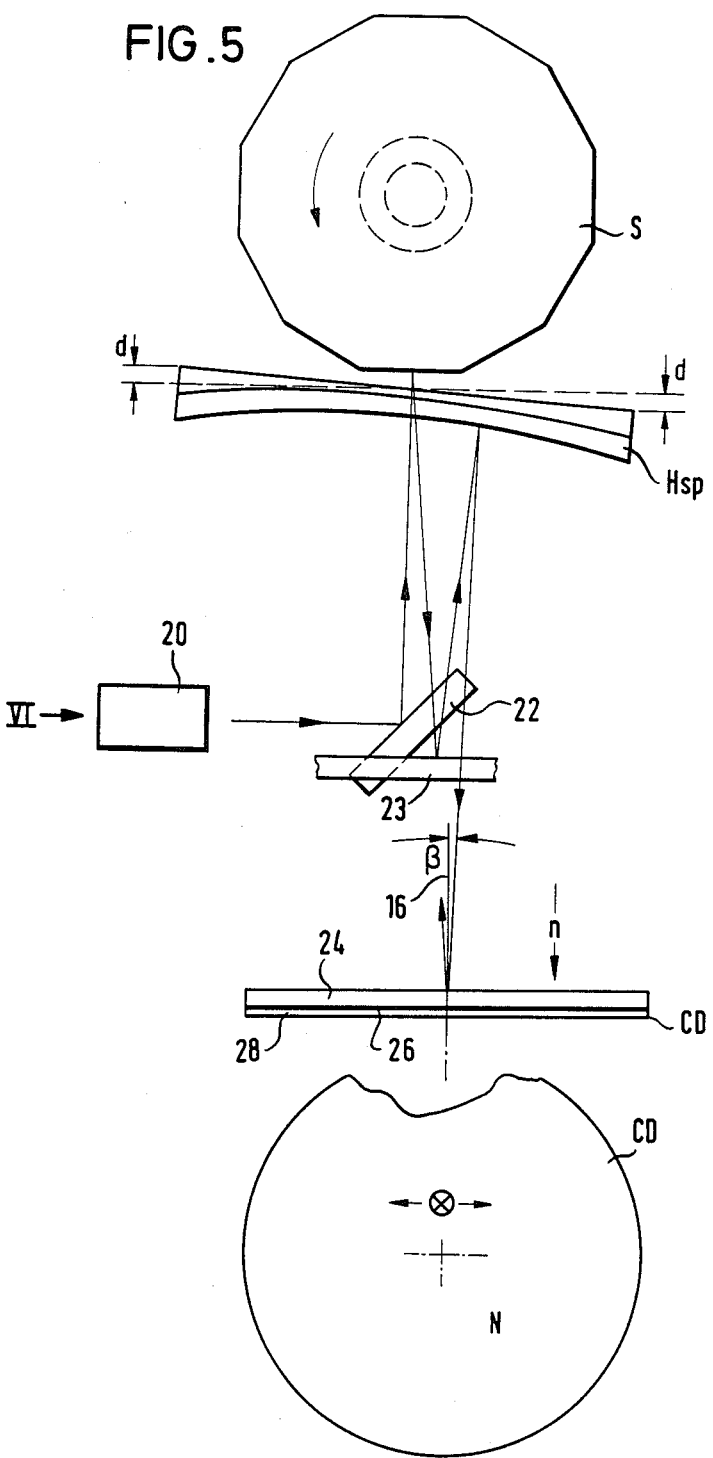
FIG. 5 shows a scanner corresponding to the variant of FIG. 3 with the view being directed onto the scanning plane.
Figure 6:
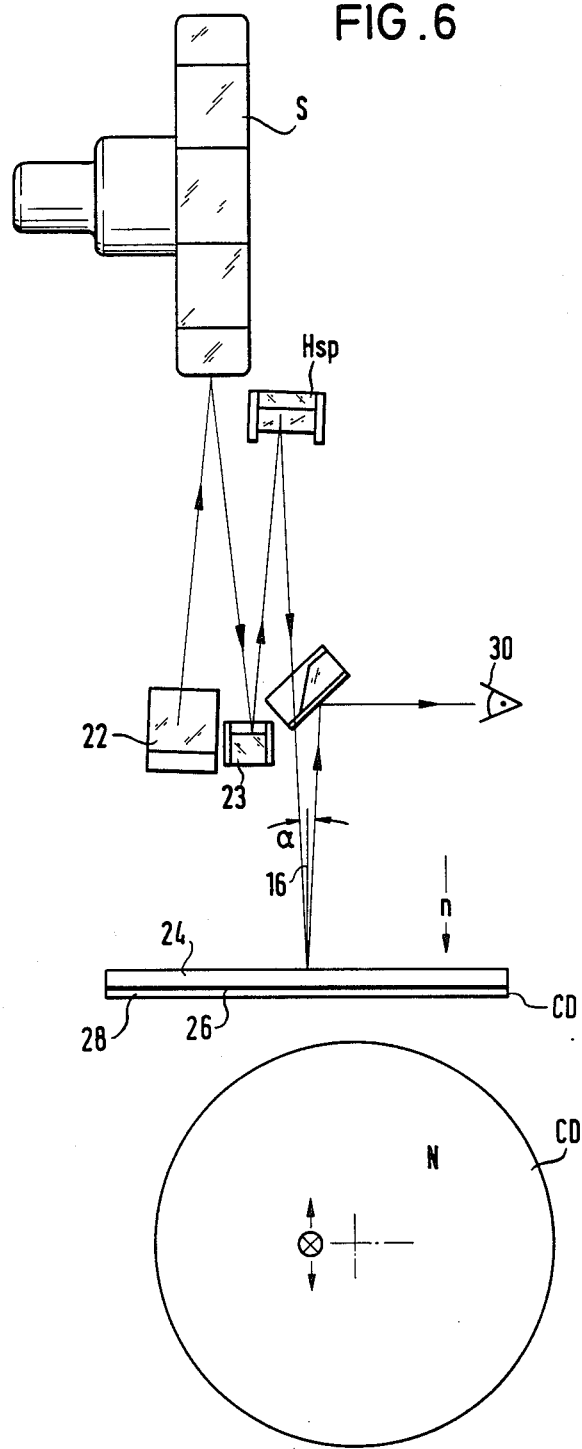
FIG. 6 shows a view of the scanner transverse to the scanning direction looking in the direction VI—VI of FIG. 5; the scan direction can be recognized by the projections n to N in FIGS. 5 and 6.
Figure 7:
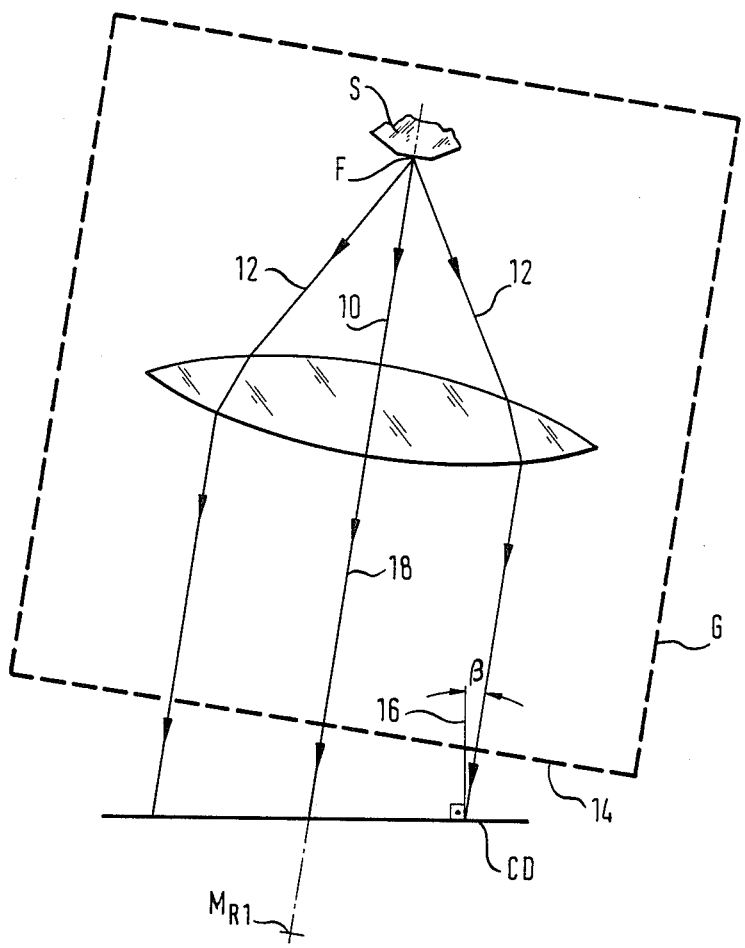
FIG. 7 shows the utilization of an objective in lieu of a concave mirror.

FIGS. 5 and 6 show further details of the basic construction of a telecentric scanner in which the concave mirror Hsp is fractionally tilted in accordance with the principle illustrated in FIG. 3. The scanner contains a laser 20 from which a laser beam is emitted and falls via an image forming optical system, which is not shown in more detail, onto a mirror 22. the direction of incidence in FIG. 6 is the viewing direction of the observer. The mirror 22 directs the reflected laser beam onto the rapidly rotating mirror wheel S. The reflected light passes via a further mirror 23 onto the concave mirror Hsp and from there onto the CD recording disc which has to be scanned. The latter consists of a carrier substrate 24, a metallic reflective layer 26 applied thereto and a covering layer 28 of transparent plastic. The light which is scattered backwardly by the CD recording disc then again enters into the scanner and is projected onto a suitable detector 30.

As one can see from FIG. 5 the concave mirror Hsp is pivoted by a small displacement stroke d relative to its position in a telecentric scanner. In this way the scanning laser beam subtends the desired small angle $\beta$ as seen in the scanning direction with a normal to the surface of the recording disc which is to be scanned. In this way the oblique incidence of the invention of the scanning light beam in the scanning direction is realized. As one can deduce from FIG. 6 the customary oblique incidence of the scanning laser beam transverse to the scanning direction is additionally provided. The optical axis of the laser beam includes a small angle $\alpha$ with the normal 16 to the surface of the recording disc to be scanned as viewed transverse to the scanning direction. This angle serves to separate the incident light and the light scattered back from the recording disc. The angle $\alpha$ is achieved in a telecentric scanner by a folded beam path transverse to the scanning direction with corresponding placement of the optical elements.

For a given scanning frequency (and thus scanning speed) and for a given rotational speed of the disc the measure for the fault width or fault length of a defect is the time during which the scanning laser beam impinges on the defect.

If the incident and the reflected beam is now in part spatially separated by an angle of incidence $\neq 0$, then the scanning laser beam is apparently larger in a fault plane above the metallic surface. Three beam regions are present, namely the incident beam, the overlap of the incident and reflected beam, and the reflected beam. This apparently larger scanning beam now impinges on a defect above the reflective metal surface of a longer period of time. For the inspection system that is precisely the same as if the finest scanning beam were to impinge at the metal surface on larger fault for the same period of time. This leads to an apparent increase in size of the fault, in particular for faults which are widely removed from the reflective metallic layer, i.e. for damage to the disc surface (read-out side).

What is claimed is:

1. A scanner for optically scanning an object having a surface, such as a recording disc, comprising:
    a coherent light source for emitting a light beam having an optical axis;
    a light deflecting device for causing the light beam emitted from the light source to sweep over the object in a substantially linear scanning movement in a scanning direction;
    an intermediate means arranged at least between the deflecting device and the object; and
    a detector for detecting light which is reflected back from the object;
    said intermediate means directing the optical axis of the light beam which subtends a small angle with a normal to the surface of the object, said subtended angle producing first and second inclined angles which are projections of the subtended angle onto first and second perpendicular planes containing the normal, at an impingement point, to the surface of the object, the first inclined angle extending in the scanning direction and the second inclined angle extending in a direction transverse thereto.

2. A scanner according to claim 1, wherein the optical axis of the light beam subtends a maximum angle of 3° with a normal to the surface of the object in the scanning direction.

3. A scanner according to claim 1, wherein the light deflecting device includes a rotationally driven polygonal mirror wheel having peripheral mirror surfaces, and wherein said intermediate means includes a concave mirror having a focal point, the concave mirror situated in a beam path between the mirror wheel and the object.

4. A scanner according to claim 3, wherein the concave mirror is a concave mirror strip having a spherical concave mirror surface.

5. A scanner according to claim 3, wherein the concave mirror is a concave mirror strip having a regular cylindrical concave mirror surface.

6. A scanner according to claim 3, wherein, in a telocentric arrangement, the effective mirror surface of the mirror wheel lies at said focal point, and the scanner as a whole is disposed at an angle in the scanning direction relative to the object.

7. A scanner according to claim 3, wherein, in comparison to a telecentric arrangement, the concave mirror is inclined, about an axis parallel to an axis of rotation of the mirror wheel, at a small angle in the scanning direction relative to the mirror wheel.

8. A scanner according to claim 3, wherein, in comparison to a telecentric arrangement, the concave mirror is displaced parallel to the scanning direction relative to the mirror wheel.

9. A scanner according to claim 1, wherein said intermediate means includes an objective including at least one lens.

* * * * *